US008183531B2

(12) United States Patent
Chinn et al.

(10) Patent No.: US 8,183,531 B2
(45) Date of Patent: May 22, 2012

(54) SYSTEM AND METHOD FOR TOMOGRAPHY COMBINING SINGLE AND PAIRED PHOTONS

(75) Inventors: Garry Chinn, San Mateo, CA (US); Craig S. Levin, Palo Alto, CA (US); Angela M. Foudray, San Jose, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 12/154,206

(22) Filed: May 21, 2008

(65) Prior Publication Data

US 2009/0072156 A1  Mar. 19, 2009

Related U.S. Application Data

(60) Provisional application No. 61/931,177, filed on May 21, 2007, provisional application No. 60/931,178, filed on May 21, 2007.

(51) Int. Cl.
*G01T 1/166* (2006.01)
(52) U.S. Cl. ............ 250/363.04; 250/252.1; 250/361 R; 250/362; 250/363.01; 250/363.02; 250/363.03; 250/369; 250/371; 250/391
(58) Field of Classification Search ............... 250/252.1, 250/361 R, 362, 363.01, 363.02, 363.03, 250/363.04, 369, 371, 391
See application file for complete search history.

(56) References Cited

U.S. PATENT DOCUMENTS

| 6,303,935 | B1 * | 10/2001 | Engdahl et al. | .......... 250/363.03 |
| 2005/0207526 | A1 * | 9/2005 | Altman | .......................... 378/20 |
| 2006/0138332 | A1 * | 6/2006 | Bryman | ................... 250/363.03 |
| 2009/0072156 | A1 | 3/2009 | Chinn et al. | |
| 2009/0078876 | A1 | 3/2009 | Chinn et al. | |

FOREIGN PATENT DOCUMENTS

WO  WO 2006/039494  4/2006

OTHER PUBLICATIONS

Braem, Chamizo Llatas, Chesi, Correia, Garibaldi, Joram, Mathot, Nappi, Riberio da Silva, Schoenahl, Seguinot, Wieilhammer, and Zaidi, "Feasibility of a novel design of high resolution parallax-free Compton enhanced PET scanner dedicated to brain research," *Phys. Med. Biol.* vol. 49, 2547-2562 (2004).

(Continued)

*Primary Examiner* — David Porta
*Assistant Examiner* — Hugh H Maupin
(74) *Attorney, Agent, or Firm* — Greer Burns & Crain Ltd

(57) ABSTRACT

Methods and systems for producing an image. Measurement data is obtained for a coincidence photon event, and a line projector function is generated based on the obtained measurement data. Additional measurement data is obtained for a single photon event, and a cone-surface projector function is generated based on the additional measurement data. An image is reconstructed using the generated line projector function and the generated cone-surface projector function. In another example method for producing an image, a measurement is obtained, and a projector function is generated using the obtained measurement. The generated projector function is modified based on an a priori image. An image is reconstructed using the modified projector function.

20 Claims, 15 Drawing Sheets

(5 of 15 Drawing Sheet(s) Filed in Color)

OTHER PUBLICATIONS

Burdette, Chesi, Clinthorne, Honscheid, Huh, Kagen, Lacasta, Llosa, Mikuz, Park, Rogers, Studen, Weilhammer, "First Results from a Test Bench for Very High Resolution Small Animal PET using Solid-State Detectors," IEEE NSS-MIC, Puerto Rico, 2376-2380 (2005).

Chinn, G., Foudray, A., Levin, C., "Accurately Positioning and Incorporating Tissue-Scattered Photons into PET Image Reconstruction." 2006 IEEE Nuc. Sci. Symp. Conf. Rec., 1746-1751 (2006).

Chinn, G., Foudray, A., Levin, C., "A Method to Include Single Photon Events in Image Reconstruction for a 1 mm Resolution PET System Built with Advanced 3-D Positioning Detectors." 2006 IEEE Nuc. Sci. Symp. Conf. Rec., 1740-1745 (2006).

Chinn, G., Levin, C., "PET Image Reconstruction with a Bayesian Projector for Multi-Electronic Collimation Schemes." 2007 IEEE Nuc. Sci. Symp. Conf. Rec., 2799-2802 (2007).

Dogan, Wehe, and Akcasu, "A Source Reconstruction Method for Multiple Scatter Compton Cameras," IEEE Trans. Nuc. Sci., vol. 39, No. 6, 1427-1430 (1992).

Du, He, Knoll, Wehe, and Li, "Evaluation of a Compton scattering camera using 3-D position sensitive CdZnTe detectors," SPIE Conf. on Hard X-Ray, Gamma-Ray and Neutron Detector Physics, Denver, CO, SPIE vol. 3768, 228-238 (Jul. 1999).

Gillam, Beveridge, Lewis, "Positron Emission Imaging using Acquired Cone-Surfaces from Opposing Compton Cameras," 2004 IEEE Nuc. Sci Symposium Conf. Rec., vol. 5, 2810-2814 (2004).

Lehner, He, Zhang, "$4\pi$ Compton Imaging using a 3-D Position-Sensitive CdZnTe Detector via Weighted List-Mode Maximum Likelihood," IEEE Trans. Nuc. Sci., vol. 51, No. 4, 3691-3694 (2004).

Parra, L., Barrett, H., "List-Mode Likelihood: EM Algorithm and Image Quality Estimation Demonstrated on 2-D PET." IEEE Trans. Med. Imaging, vol. 17(2), 228-235, Apr. 1998.

Singh, "An electronically collimated gamma camera for single photon emission computed tomography. Part I: Theoretical considerations and design criteria," Med. Phys., vol. 10(4), 421-427 (Jul./Aug. 1983).

Singh and Doria, "An electronically collimated gamma camera for single photon emission computed tomography. Part II: Image reconstruction and preliminary experimental measurements," Med. Phys., vol. 10(4), 428-435 (Jul./Aug. 1983).

Tai, Laforest and Ruangma, "Design Study of a Detector Insert for High-Resolution Clinical PET Imaging," Conf Proc. IEEE NSS-MIC, Portland, 1714-1717 (2003).

Wilderman, Clinthorne, Fessler, Hua, Rogers, "List-Mode Maximum Likelihood Reconstruction of Compton Scatter Camera Images in Nuclear Medicine," Proceedings of the 1998 IEEE Nuclear Science Symposium, vol. 3, 1716-1720 (1998).

* cited by examiner

Phantom 1

Phantom 2

SYSTEM AND METHOD FOR TOMOGRAPHY COMBINING SINGLE AND PAIRED PHOTONS

PRIORITY CLAIM AND REFERENCE TO RELATED APPLICATION

The present application claims the benefit of U.S. Provisional Application Ser. No. 60/931,177, filed May 21, 2007, and U.S. Provisional Application Ser. No. 60/931,178, filed May 21, 2007, under 35 U.S.C. §119, which are incorporated in their entirety by reference herein.

STATEMENT OF GOVERNMENT INTEREST

This invention was made with Government assistance under National Institutes of Health (NIH) Grant Nos. CA119056 and EB003283. The Government has certain rights in the invention.

This application is also related to co-pending application Ser. No. 12/154,261, entitled "METHOD AND SYSTEM FOR USING TISSUE-SCATTERED COINCIDENCE PHOTONS FOR IMAGING", filed on even date herewith.

FIELD OF THE INVENTION

The invention relates generally to the field of high-resolution imaging.

BACKGROUND OF THE INVENTION

In tomography, measurements are taken though multiple views of a subject (e.g., human or animal in biomedical applications), and mathematical algorithms are used to convert these measurements into three-dimensional (3-D) images of the subject. Such algorithms are referred to as tomography image reconstruction algorithms.

Example tomography image reconstruction algorithms can be performed by successive approximation methods, such as iterative maximum likelihood (ML) expectation-maximization algorithms. In an iterative ML algorithm, an image is updated using a gradient-based function at each iteration. The gradient function is calculated using a forward projection function, which describes how the 3-D image maps to the data space.

However, this forward projection is mathematically ill-posed. For example, noise in the measurements is amplified by the image reconstruction algorithm, degrading the image quality. Filtering can reduce the noise, but at the expense of image resolution and contrast.

An example imaging technique is positron emission tomography (PET). Generally, in PET and similar imaging methods, radioactive isotopes are injected into a subject. Decay of the isotopes (that is, a positron-electron annihilation event) results in photons being emitted from inside the animal. In conventional PET, detectors positioned outside the animal detect emitted photon pairs when they hit the detectors. These interactions are recorded, including the detection location and the energy. Based on these recorded interactions, an image of where the radioactive isotope is distributed in the body can be imaged using a tomography image reconstruction algorithm. PET is a widely used clinical imaging procedure for applications such as, but not limited to, staging and monitoring disease in cancer patients.

Conventionally, emitted photons from a source that are detected in coincidence by the detectors are used to reconstruct the 3-D tomographic images. So-called true coincidence events are assumed to have occurred somewhere along the line between two photons detected within a preset coincidence time window. Thus, a line can be determined between the photon pair based on the location of the detected photons, and the determined lines can be used to construct the image.

However, a large majority of the events detected by the detectors are not true coincidence events, but rather single photon events. It has been estimated that single-photon events make up about 90% of all detected events in a human PET system. Conventional PET systems do not use these single photon events to produce images. Alternate detector designs can be used to produce images from single photons. However, single photons do not provide images of the same resolution as that of coincidence photons, even though there are more single photon events. Thus, conventional PET systems ignore single photon events, and large amounts of available information remain unused, reducing the signal-to-noise ratio of the reconstructed image.

SUMMARY OF THE INVENTION

Embodiments of the present invention provide, among other things, methods and systems for producing an image. In an example method, measurement data is obtained for a coincidence photon event, and a line projector function is generated based on the obtained measurement data. Additional measurement data is obtained for a single photon event, and a cone-surface projector function is generated based on the additional measurement data. An image is reconstructed using the generated line projector function and the generated cone-surface projector function.

In another example method for producing an image, a measurement is obtained, and a projector function is generated using the obtained measurement. The generated projector function is modified based on an a priori image. An image is reconstructed using the modified projector function.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 9A shows a reconstructed image using only coincidence data, FIG. 9B shows a reconstructed image using simultaneous data channels, FIG. 9C shows a reconstructed image using sequential data channels, and FIG. 9D shows a reconstructed image using a Bayesian projector approach;

FIG. 10A shows a mean reconstructed image using only coincidence data, FIG. 10B shows a mean reconstructed image using simultaneous data channels, FIG. 10C shows a mean reconstructed image using sequential data channels, and FIG. 9D shows a mean reconstructed image using a Bayesian projector approach;

FIG. 15A shows phantom 1 with a 9:1 sphere:cylinder activity ratio, and FIG. 15B shows phantom 2 with three columns of each size sphere, where the outer columns have a 9:1 sphere:cylinder activity ratio, the middle columns have a 5:1 sphere:cylinder activity ratio, and the innermost have a 3:1 sphere:cylinder activity ratio;

FIG. 16A shows an OS-EM algorithm using only coincidence events for reconstructing the image, and FIG. 16B shows a list-mode OS-EM algorithm used to combine coincidence and single photons;

FIG. 17A shows an OS-EM algorithm using coincidence events, and FIG. 17B shows an OS-EM algorithm using a Bayesian projector for Compton collimation and a standard projector for coincidence events;

FIGS. 18A-18B are plots of sphere signal-to-noise (SNR) vs. contrast ratio for different iteration subsets for coincidence reconstruction and combining coincidence and singles reconstruction using the Bayesian projector, wherein FIG. 18A shows 5 to 1, 1.5 mm spheres, and FIG. 18B shows 10 to 1, 1.75 mm spheres; FIG. 19A shows 5 to 1, 1.5 mm spheres and FIG. 19B shows 10 to 1, 1.75 mm spheres.

DETAILED DESCRIPTION

Figure 1:
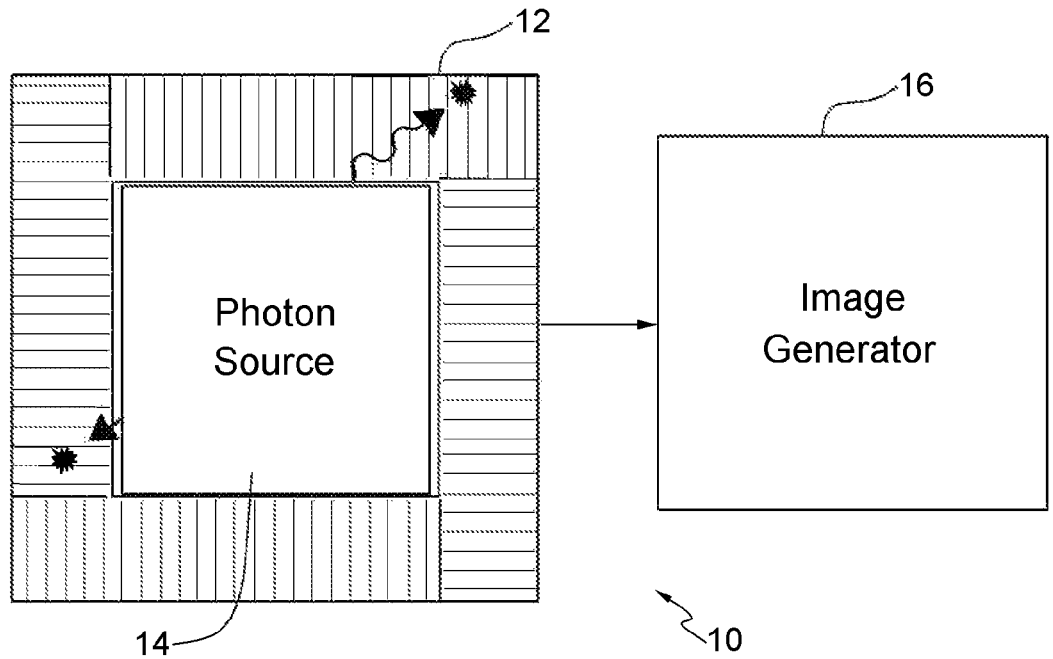
FIG. 1 shows an imaging system according to an embodiment of the present invention.

In PET, coincidence events may be used to provide image information by using coincidence measurements. That is, PET systems conventionally determine a line between a pair of detected photons (coincidence collimation), along which line the position of a decay event in tissue is determined to occur. However, single detected photons have been discarded in conventional PET systems, though they provide the large majority of detected events. Example embodiments of the present invention use both single photon events and coincidence photon events to produce 3-D tomographic images. Single photon events are incorporated into the set of usable events via Compton kinematics collimation.

Compton kinematics collimation is an imaging method that uses the kinematics of Compton scatter (Compton kinematics). In a typical example of so-called Compton PET, a Compton camera uses a scattering layer and an absorption layer, and produces images from measurements of single photons. By recording the position and energy of a Compton interaction in the scatter layer and a photoelectric interaction in the absorption layer, the Compton kinematics can position the decay event somewhere on a cone-surface.

In an example of Compton kinematics collimation, the energies and positions of individual interactions are measured in a 3-D detector and used to calculate the direction of each individual photon. The decay event is then localized to the surface of a cone based on Compton kinematics.

However, Compton kinematics collimation conventionally has suffered from poor angular blurring due to Doppler broadening, energy blurring, and position blurring. Thus, the reconstructed spatial resolution of Compton kinematics collimation is limited compared to coincidence collimation. Combining Compton kinematics collimation with coincidence collimation to produce better images is a challenging problem because of this large resolution mismatch. According to example methods of the present invention, these two measurements can be combined to improve overall image quality and/or quantification.

Hybrid Compton PET systems using two Compton cameras with coincidence capability have also been proposed. Such systems are able to perform both conventional coincidence PET imaging and Compton kinematics imaging. Some three-dimensional (3-D) PET detectors also have the ability to function as a coincidence detector and as a Compton camera. A 3-D detector can perform coincidence Compton kinematics collimation on single photons if it can precisely measure the position and energy of individual interactions in the detector.

In an example embodiment of the present invention, a PET system and method is provided in which 3-D detectors are used to perform two types of electronic collimation: coincidence collimation and Compton kinematics collimation. In this way, the data form different channels, including a coincidence collimation channel and a Compton kinematics collimation channel. An example reconstruction algorithm combines these two channels to provide image reconstruction and detection and produce a 3-D tomographic image. Example embodiments of the present invention also account for the large resolution mismatch between coincidence collimation and Compton kinematics collimation.

Using coincidence collimation and Compton kinematics collimation, an example PET system can image both coincidence photon pairs and single photons. Thus, example methods and systems can recover many additional events not used by current PET methods, increasing the statistics of the data set and potentially improving the image quality and/or quantification. Example embodiments also provide both benefits of coincidence photons (e.g., higher resolution) and single photons (higher signal-to-noise ratio).

In an example method for producing an image of a subject according to the present invention, measurement data is obtained for a coincidence photon event, and a line projector function is generated based on the obtained measurement data, providing a coincidence collimation channel. Additional measurement data is obtained for a single photon event, and a single photon projector function, such as a cone-surface projector function, is generated based on this additional measurement data to provide a Compton kinematics collimation channel. By combining the data from the coincidence collimation channel and the Compton kinematics collimation channel, an image of the subject is reconstructed using the generated line projector function and the generated cone-surface projector function.

An example projector function for coincidence photons is the line between the two detectors that recorded the photons. An example Compton kinematics cone-surface projector function estimates the incoming direction of photons using Compton kinematics within the detector.

More particularly, to calculate a Compton kinematics cone-surface projector function, multiple interactions in the detector for a single photon event are detected, including the interaction position and energy. The incident angle on the photon can be estimated using the measured interaction position and energy, for example, for the first two interactions in the detector. A cone-surface projector function is then formed. However, more than two interactions may be used.

To calculate the projection function for coincidence photons, an example imaging system and method may calculate a line projector function. Methods for calculating a line projector function for coincidence events will be understood by those of ordinary skill in the art.

These separate data channels can be combined using any of various techniques in so-called multi-channel tomography for image reconstruction. The coincidence events form one data channel with high-reconstructed spatial resolution. The non-coincident singles events form a second channel with low-reconstructed spatial resolution. The objective then becomes combining these channels to produce an image with superior quality in terms of contrast, resolution, and/or signal-to-noise ratio. Nonlimiting example reconstruction methods are provided according to embodiments of the present invention, including using simultaneous data channels, using sequential data channels, and using a Bayesian projector function. It will be understood that variations on the algorithms described herein are possible according to various embodiments of the present invention.

In an example method using simultaneous data channels, a data vector is formed including a combination of coincidence and non-coincident single events, and a system matrix is formed using discrete approximations of reconstruction models for the two channels. In an example use of sequential data channels, starting from a uniform image, an ordered-subsets expectation maximization (OS-EM) algorithm is performed using only non-coincident singles data, and iterations are then continued using only coincidence data.

Other example methods and systems use a Bayesian projector function with non-uniform emission probability along a line of response that is weighted by an a priori image generated from the low-resolution (Compton kinematic collimation) channel to reconstruct the high-resolution (coincidence) channel, or vice versa. Another image reconstruction method uses priors generated by reconstructing images from high-spatial resolution coincidence data followed by post-reconstruction smoothing to provide imaging.

Generally, an imaging system according to example embodiments of the present invention includes a plurality of 3-D detectors capable of measuring the interaction position (e.g., in three dimensions) and energies of individual photons emitted from a source, and a device or system for image reconstruction coupled to the one or more detectors. Examples of sources of emitted photons will be known to those of ordinary skill in the art. A nonlimiting example source of emitted photons is animal tissue into which radioactive isotopes have been injected. The 3-D detectors are disposed with respect to the source of emitted photons to receive the emitted photons and produce interactions. The emitted photons include single photons and coincidence photons.

The one or more detectors may include, as nonlimiting examples, 3-D PET detectors and Compton cameras used in coincidence. Other suitable detectors capable of measuring the position (in three dimensions) and energies of individual photons emitted from the source may be used. Such 3-D detectors have the ability to function as a coincidence detector and as a Compton camera, and can perform coincidence kinematics collimation. Nonlimiting examples of PET systems include systems having 3-D positioning cadmium-zinc-telluride (CZT) detectors. An example CZT detector is described in International Patent Application No. PCT/US2005/035203, filed Sep. 30, 2005, which is incorporated in its entirety by reference herein.

An image generator (that is, a device or system for image reconstruction) is coupled to the 3-D detectors to receive a position and energy for the produced interactions and reconstruct an image. The image generator is configured to generate a line projector function based on the coincidence photons and a cone-surface projector function based on the single photons. The image generator is further configured to reconstruct an image using the generated line projector function and cone-surface projector function.

Examples of image generators include a computing device (as a nonlimiting example, a PC or group of connected PCs) suitable for running an image reconstruction algorithm, which may be implemented in software, hardware, firmware, loaded via suitable media, etc. A computing device may include a suitable processor or processors, memory, input devices, storage devices, output devices (such as, but not limited to, printers, monitors, network outputs, etc.), configured to receive inputs directly or indirectly from the one or more detectors via any suitable connection. According to example embodiments of the present invention, the computing device is configured to implement the image reconstruction algorithm. Thus, additional embodiments of the present invention may be provided in a computing device configured to perform methods of the present invention and/or a computer-readable medium, a propagated signal, firmware, software, etc., capable of causing a computing device to perform a method of the present invention.

It will be appreciated that various PET systems, including various commercial PET systems, capable of 3-D positioning may be used as the one or more detectors and image generator if configured to implement example image reconstruction algorithms according to the present invention. Generally, the effectiveness of any such system will at least partly depend on the 3-D positioning resolution and energy resolution of the detectors used.

Embodiments of the present invention that image using coincidence photons and single photons can improve the sensitivity, image quality, and/or quantification of PET. Example embodiments can reduce scan times, increasing patient throughput and reducing per-scan costs (and potentially radioactive dosage delivered to the patient). Embodiments of the present invention may also be used to perform simultaneous measurements of PET and SPECT (single photon emission computed tomography) isotopes.

Preferred embodiments will now be discussed with respect to the drawings. The drawings include schematic figures that are not to scale, which will be fully understood by skilled artisans with reference to the accompanying description. Features may be exaggerated for purposes of illustration. From the preferred embodiments, artisans will recognize additional features and broader aspects of the invention.

FIG. 1 shows an example imaging system 10. The imaging system 10 includes a plurality of 3-D detectors 12 disposed with respect to a source 14 of emitted photons. A nonlimiting example 3-D PET detector 12 is a 3-D cadmium zinc telluride (CZT) cross-strip detector. It will be understood, however, that methods and systems of the present invention are also generally applicable to other 3-D detectors or Compton cameras with coincidence capabilities. Semiconductor detectors, such as CZT detectors, have an intrinsic resolution that is set by the pitch of an electrode pattern deposited on the detector faces, rather than by using arrays of crystal rods. Semiconductor detectors directly collect the charge deposited by photon interactions, versus relying on scintillation light creation, transport, collection, and photodetector conversion.

These 3-D detectors 12 are suitably coupled to an image generator 16, which receives signals from the 3-D detectors and processes the signals to generate an image. Examples of suitable couplings will be understood by those of ordinary skill in the art, including but not limited to electrical and optical couplings. Examples of suitable image generators 16 are described above. It is not required that the image generator 16 be co-located with the 3-D detectors 12, but instead the image generator may be located anywhere that signals from the 3-D detectors may be received.

Principles of example image reconstruction algorithms according to embodiments of the present invention will now be explained. In conventional PET, images are reconstructed from coincidence events, which occur when exactly two photons are detected within a time coincidence window. The projector function for a coincidence event is the line between the two detectors that recorded the photons.

Figure 2:
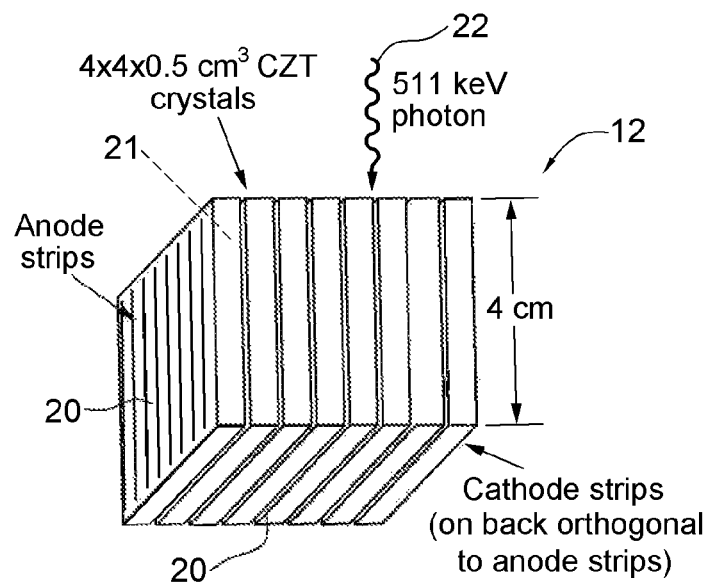
FIG. 2 shows an example individual 3-D detector.

A 3-D PET detector such as the CZT detector 12, which can measure the position and energy of individual interactions, can use Compton kinematics to calculate a Compton kinematics cone-surface projector function for non-coincident single photons. FIG. 2 shows an example individual 3-D detector 12. In the CZT detector 12, orthogonal anode and cathode cross strip electrodes 20 disposed over a CZT crystal 21 are used to sample the interaction position of a photon 22 along two dimensions. The position of the interaction in the third dimension is computed from the anode-to-cathode signal ratio.

As a nonlimiting example, a 1 mm×1 mm×1 mm spatial resolution can be achieved by using 1 mm pitch anode and cathode orthogonal cross strips. The cross strip electrodes 20 provide effective detection elements that can resolve individual Compton scatter and photoelectric interactions within the detector with high energy resolution. In an example CZT detector, energy resolution has been measured at ≦2.5% FWHM for 511 keV photons. With high depth of interaction (DOI) resolution, the example detectors 12 may be brought in as close as desired for higher solid angle coverage and photon sensitivity. Further, example cross-strip designs allow a significant reduction in readout channels (e.g., 2n vs. $n^2$) compared to an electrode design that achieves the same intrinsic resolution using an anode that includes a 2-D matrix of small square pixels.

As shown in the example system of FIG. 1, the CZT detectors 12 may be stacked in an edge-on configuration. This allows incoming photons to encounter a minimum of multiple centimeters of detector material for high photon sensitivity. The edge-on orientation further facilitates better coincidence time resolution, since the best timing performance occurs when the electron drift distance (orthogonal to electrode planes) is short and is generally better for thinner slabs. Reducing the thickness of the detector may reduce the effects of carrier drift time, but it will also increase the device capacitance, which also degrades time resolution for CZT (since there is no charge amplification). Performance of the detector will be affected by photon scatter between neighboring detector elements and the detector's Compton scatter performance. Example CZT detectors 12 provide high intrinsic detection efficiency and facilitate coupling to readout electronics.

With a minimum photon traversal distance of 4 cm, the single 511 keV photon detection efficiency is roughly 86% (74% for two photons in coincidence). To preserve high photon sensitivity, if a multi-interaction photon event occurs, the event energy is determined by summing charge deposited on any detector's strips within a localized region that is above a pre-defined threshold.

The example detector 12 configuration and arrangement can operate both in coincident photon and Compton collimation (single photon) detecting mode. Example methods of the present invention apply these modes to provide separate data channels for reconstructing images.

Figure 3:
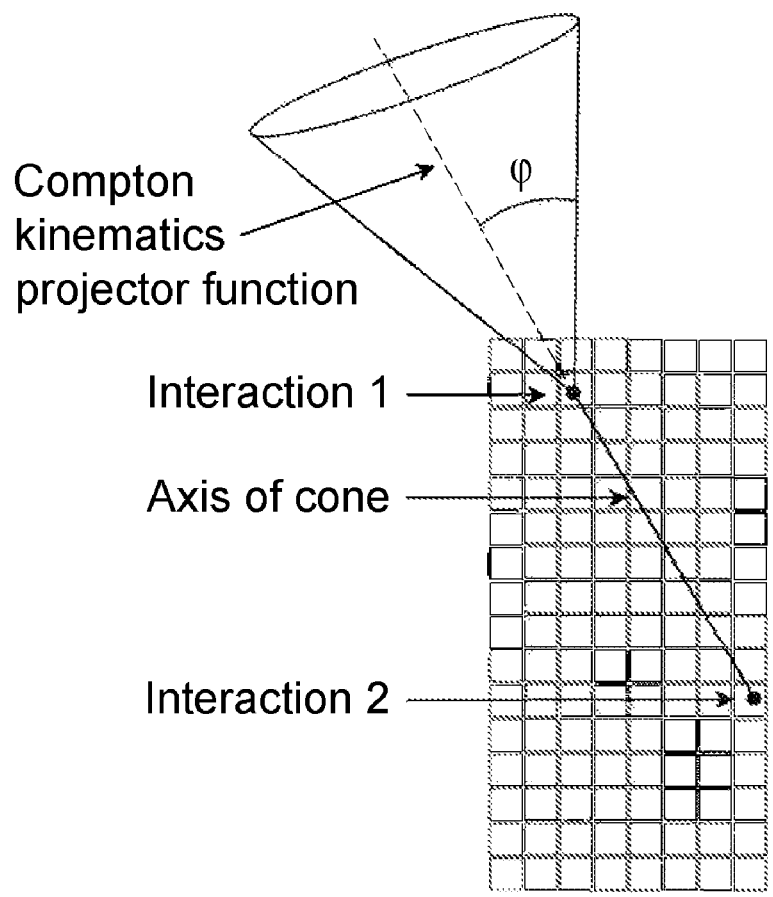
FIG. 3 is a schematic diagram illustrating Compton kinematics for the 3-D CZT detector of FIG. 2.

FIG. 3 illustrates how a high-resolution 3-D detector can calculate the incident angle of a single photon event. The incident angle of the photon can be estimated when the position and energy of the first two interactions in the detector are measured. Monte Carlo simulations suggest that 70% of all detected events involve two or more interactions in the detectors. A cone-surface projector function can be formed for the single photon event where the line formed by the two interactions from the cone axis and the cone half angle φ is calculated by $$\cos\varphi = 1 - m_e c^2 \left( \frac{1}{E_1} - \frac{1}{E_0} \right) \quad (1)$$

where $E_0$ is the incident photon energy and $E_1$ is the photon energy after the first Compton interaction in the detector, $m_e$ is the mass of an electron, and c is the speed of light. Doppler broadening, energy blurring, and spatial blurring in the 3-D detector leads to angular blurring of the cone half angle φ. Compton collimation is described further in, for example, D. B. Everett, J. S. Fleming, R. W. Todd, and J. M. Nightingale, "Gamma-radiation imaging system based on the Compton effect," Proc. IEE, vol. 124, pp. 995-1000, 1977; M. Singh, "An electronically collimated gamma camera for single photon emission computed tomography, part I: theoretical considerations and design criteria," Med. Phys., vol. 10, pp. 421-427, 1983; and M. Singh and D. Doria, "An electronically collimated gamma camera for single photon emission computed tomography, part II: Image reconstruction and preliminary experimental measurements," Med. Phys., vol. 10, pp. 428-435, 1983.

The forward model for reconstructing these single events is given as $$s(y_i, \phi_i) = \int_C p(\phi_i, y_i, x) f(x; T) dx \quad (2)$$

where $f(x) \equiv f(x;T)$ is a random variable corresponding to the number of photons generated over the total scan time T at the point x and $p(\phi_i, y_i, x)$ is the probability of an emission from position x in tissue detected at $y_i$ and incident angle $\phi_i$. Additional interactions (e.g., three or more) can result in additional information derived via Compton kinematics.

By contrast, in conventional PET, a coincidence event occurs when exactly two photons are detected in the photopeak energy window and coincidence time window. For example, let $y_{kl}$ correspond to the k-th and l-th detector pair, then the counts recorded for this pair is given by $$o(y_{kl}) = \int_L p(y_{kl}, x) f(x; T) dx \quad (3)$$

where $f(x) \equiv f(x;T)$ is a random variable corresponding to the number of photons generated over the total scan time T at the point x and $p(y_{kl},x)$ is the fraction of annihilation events at position x in tissue that result in a pair of photons detected in coincidence recorded at the detector pair $y_{kl}$. The discrete version of equation (2) provides an example of a projector function for single photon events, whereas the discrete version of equation (3) provides an example of a projector function for coincidence events.

Figure 4:
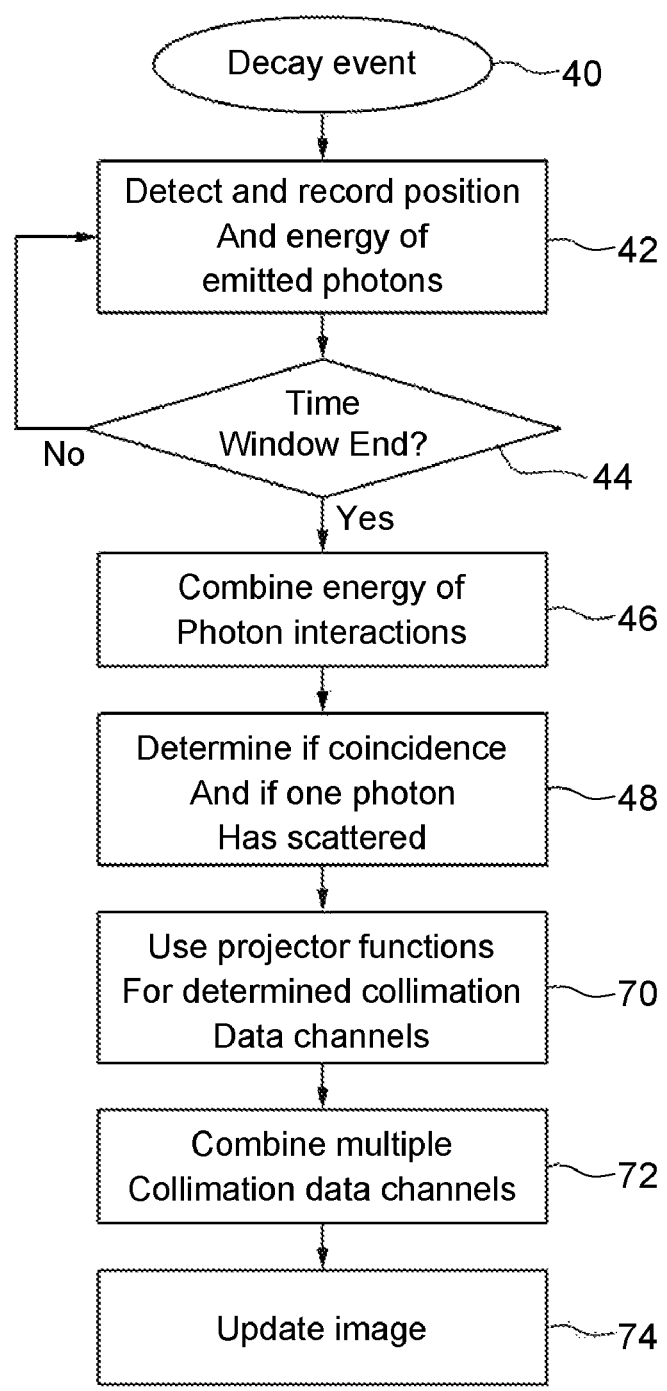
FIG. 4 shows an example imaging method using both single photon events and coincidence events, according to an embodiment of the present invention.

FIG. 4 shows an example imaging method for embodiments of the present invention using projector functions for both single photon events and coincidence events. In an example imaging method, the emitted photon source 14 generates annihilation photons in pairs, which may be detected by the 3-D detectors 12. For example, during a decay event (step 40), measured using a preset coincidence time window, emitted photons are detected (step 42) as photon interactions within the one or more detectors, and at least one position (individual location) and energy of interaction is recorded. When the time window is completed (step 44), the energy of recorded photon interactions within the time window is combined (step 46) (as a nonlimiting example, summed), and a determination is made (step 48) as to whether a photon pair (a coincidence) has been detected and if so, whether one of the detected photon pair is scattered.

Figure 5:
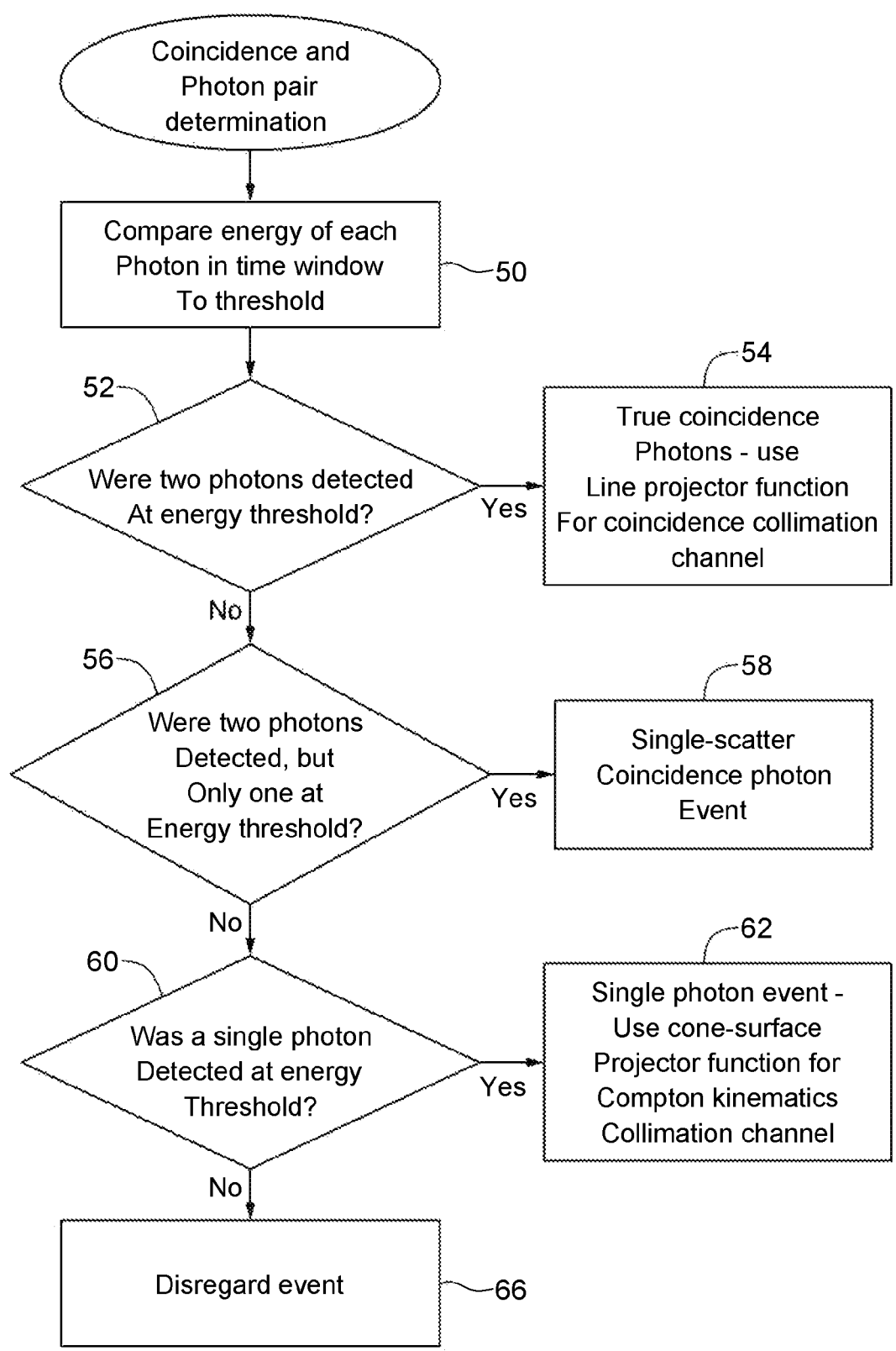
FIG. 5 shows an example method for determining whether a coincidence event or a single photon event is present.

Preferably, as shown in FIG. 5, a determination is made based on the combined amount of interaction at a particular detector location within the time window by comparing (step 50) the energy to a threshold. As a nonlimiting example, for photons detected in coincidence, photon interaction may take place at two distinct detector locations. If, within the time window, two photons are detected, each having combined photon interaction energy of, for example, 511 keV, or within a predetermined window surrounding 511 keV (step 52), it is determined (step 54) that coincidence photons have been detected.

If coincidence photons are detected, but one of the photons has combined photon interaction energy of less than 511 keV, or is outside the predetermined window (step 56), then in some example embodiments it may be determined (step 58) that a single-scatter coincidence event occurred (i.e., that one of the pair of photons scattered in tissue). In an example embodiment, such single-scatter coincidence photons may be processed according to methods described in application Ser. No. 12/154,261, entitled "METHOD AND SYSTEM FOR USING TISSUE-SCATTERED COINCIDENCE PHOTONS FOR IMAGING", filed on even date herewith. In other example embodiments, scattered photons may be discarded.

However, if a single photon is detected, with combined photon interaction energy of 511 keV, or within a window surrounding 511 keV (step 60), a single photon event is determined (step 62). If, on the other hand, a single photon, or both of a pair of coincidence photons, is detected with a combined photon interaction energy of less than 511 keV (or an energy outside a predetermined window), the event may be discarded (step 66).

Given the detected interactions in the detectors, including the interaction position and energy, projector functions are used to provide collimation data channels (step 70). For example, if a coincidence event is determined (step 54), a line projector function may be produced based on the interaction location and energy for the two detected photons, providing a coincidence collimation data channel. If, on the other hand, a single photon event is determined (step 62), a cone-surface projector function may be produced based on the interaction location and energy for two or more interactions in a detector, providing a Compton kinematics collimation data channel. The coincidence collimation channel data and the Compton kinematics collimation channel data are combined (step 72), and an image is reconstructed (step 74), providing multi-channel tomography. The combining may take place before or during image reconstruction.

Any of various image reconstruction methods, including but not limited to list-mode, sinogram-based, histogram-based, etc., methods, can be used to reconstruct the images. In a nonlimiting example embodiment of the present invention, a list-mode (LM) algorithm is used to reconstruct the images. In the list-mode approach, a histogram of the counts is not used. Instead, the measurements $m=\{m_i\}, m_i \in \{o(y_{ij}), s(y_k, \phi_k)\}$ correspond to the sequence of individual detected events. The expectation maximization algorithm (EM) can be used to reconstruct the image with voxels $\lambda_j$ using the iteration $$\lambda_j^{l+1} = \frac{\lambda_j^l}{n_j} \sum_i \frac{m_i p_{ij}}{\sum_k p_{ik} \lambda_k^l} \quad (4)$$

where l is the previous iteration number, $n_j$ represents the sensitivity correction for the j-th voxel, and $p_{ij}$ represents the discrete weights of the projector function for the j-th voxel and measurement $m_i$. If $m_i$ is a non-coincident singles event, then $p_{ij}$ is calculated from the discrete version of equation (2). Otherwise, $m_i$ is a coincidence event, and a discrete version of equation (3) is used to form $p_{ij}$. This algorithm is readily adapted for list mode data, though equation (4) may also be implemented, for example, as a sinogram or histogram-based algorithm. Nonlimiting examples of list mode algorithms are provided in L. Parra and H. H. Barrett, "List mode likelihood: EM algorithm and image quality estimation demonstrated on 2-D PET," *IEEE Trans. Med. Imaging*, pp. 228-235, 1998; and S. J. Wilderman, N. H. Clinthorne, J. A. Fessler, C-H Hua, and W. L. Rogers, "List mode EM reconstruction of Compton scatter camera images in 3-D," *Proceedings of the 1998 IEEE Nuclear Science Symposium*, vol. 3, pp. 1716-1720, 1998.

Ordered subsets can accelerate the image reconstruction algorithm process to form a list mode ordered subset EM algorithm (LM OS-EM). In this approach, the list-mode data set is divided into S equal length data sets. The image is then updated after each subset before the next data subset is processed. Each iteration pass through the entire data set then results in S image updates, accelerating the reconstruction process. An example of ordered subsets is provided in H. M. Hudson and R. S. Larkin, "Accelerated image reconstruction using ordered subsets of projected data," IEEE Trans. Med Imaging, vol. 13, pp. 601-609, 1994.

For each list-mode count, a coincidence time window is applied followed by a clustering method to group interactions. Each cluster corresponds to the energy deposited by a single photon. Next, an energy window is used to reject photons that may have been scattered in tissue. If two clusters are accepted after the energy window, sequence estimation is used to identify the first interaction for each photon. The coincidence line projector function is used for $p_{ij}$, with the ends of the line segment positioned at the location of the first interaction for each photon.

For non-coincident single photon events, sequence estimation is used to identify the first two interactions. The first two interactions are then used to calculate the Compton kinematics projector function, forming the values of $p_{ij}$ used by equation (4).

Coincidence events form one data channel with high-reconstructed spatial resolution. The non-coincident singles events form a second channel with low reconstructed spatial resolution. Example embodiments of the present invention combine these channels to produce an image with improved quality in terms of contrast, resolution, and/or signal-to-noise ratio.

Two example methods for combining the data channels include use of simultaneous data channels and sequential data channels, respectively. In a simultaneous data channel approach, the Poisson-distributed data vector is a combination of coincidence and non-coincident singles events given by $$m = \begin{pmatrix} o(y_{ij}) \\ s(y_k, \phi_k) \end{pmatrix} \quad (5)$$

The system matrix is then formed by discrete approximations to equations (2) and (3).

In a sequential data channel approach, the coincidence and non-coincident singles events are used separately in the reconstruction process. For example, starting from a uniform image, the OS-EM algorithm is performed using only the non-coincident singles data. OS-EM iterations are then continued using only the coincidence data. Only a single iteration can be performed using this example approach.

Another approach for combining multiple collimation channels for tomographic image reconstruction is a Bayesian projector approach. Bayesian methods have been proposed that add a penalty function to increase smoothness in a maximum likelihood approach. Example Bayesian projector approaches according to embodiments of the present invention provide a projector function to improve sensitivity, image quality (e.g., as determined by signal-to-noise ratio, resolution, and/or contrast), and/or quantification by reducing the noise amplification associated with tomographic image resolution.

Generally, imaging systems such as multi-collimation PET systems have multiple methods of collimation with varying spatial resolution. One nonlimiting example is an insert system, which places high spatial resolution detectors inside a conventional PET system with collimation channels formed by coincidences between the different detector rings. Another example is a PET system, such as that described above, using high spatial and energy resolution 3-D detectors made from cadmium zinc telluride (CZT) detectors, which can collect high-resolution coincidence events (i.e., collimate photon pairs) and use Compton kinematics for low-resolution collimation of single photons.

Compton collimation of single photons can dramatically increase overall photon sensitivity by making use of events that are discarded by conventional imaging (e.g., PET) systems. However, in Compton kinematics, with current technology, angular blurring of the Compton collimation direction leads to lower spatial resolution than standard coincidence photon collimation. Reconstructing images with coincidence and single photons can provide higher effective photon sensitivity and reconstructed signal-to-noise ratio.

Example multi-collimation methods using a Bayesian projector are provided according to embodiments of the present invention. Example Bayesian projector methods are applicable to various imaging systems, including any multi-collimation PET system.

In PET, the decay of a radionuclide in a subject generates a pair of photons traveling in opposite directions along a line. Detectors surrounding the subject measure the photons (location and energy), and the projector function corresponds to the line defined by the two measured photons. This line projector function specifies the probability of the decay event occurring at various positions in 3-D space. For PET, this function is zero everywhere except at the points defined by the line. The decay probabilities are assumed to be equal at every point on this line.

In a Bayesian method according to example systems and methods of the invention, one or more priors, from any of various sources, is used to modify (e.g., re-weight) the probabilities along the line such that the probabilities are not equal everywhere along the line. The one or more priors represent the probability of a decay event as a function of 3-D space. The Bayesian projector may then be implemented by, as a nonlimiting example, multiplying the line function (probability as a function of 3-D space) with the prior (also a probability as a function of 3-D space). By contrast, current methods for radionuclide imaging assume that the probabilities along the line are uniform, which may not be as robust to noise.

Figure 6:
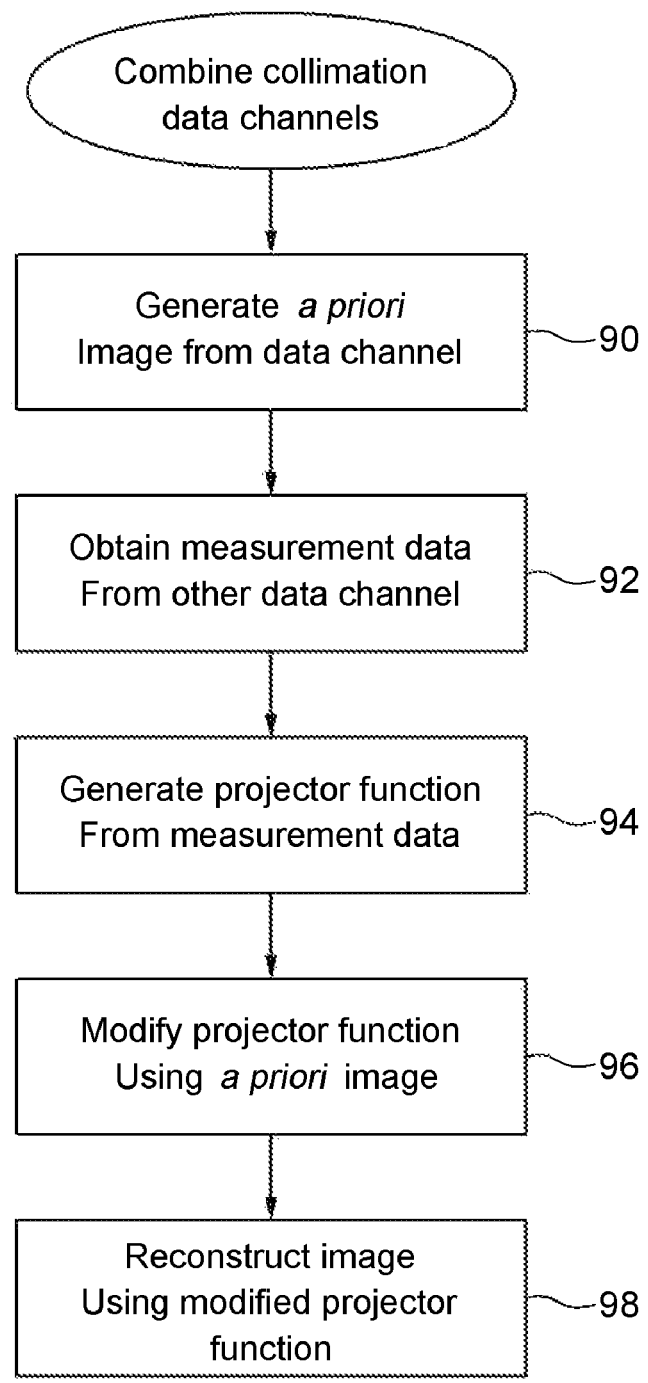
FIG. 6 shows an example method for using an a priori image for multi-collimation events, according to an embodiment of the present invention.

According to an example method of the present invention, as shown in FIG. 6 an a priori image (also referred to as a prior) is generated (step 90) for modifying a projector function. The prior may be of a different resolution, a different modality, etc. The prior may also be filtered before it is used to modify the projector function.

Example methods and systems then obtain measurement data (step 92), and generate a projector function (step 94) based on the obtained measurement. A projector function for tomography may be determined using any appropriate method. A particular example method includes measuring position and energy for photon interactions for coincidence photon events. The projector function may be determined using the measurements. For example, a line between the detection locations for the coincidence photon events may provide the projector function.

The projector function is modified using the a priori image(s) (step 96), and an image is reconstructed (step 98) using the modified projector function. For example, using a Bayesian projector function, the line projector function may be multiplied by the a priori image to modify the function. More particular example methods for modifying the projector function are described below. Various imaging processing methods and/or imaging modalities can be used to improve the performance of the Bayesian projection function by improving the modeling accuracy of the prior image.

A system for performing Bayesian methods according to embodiments of the present invention includes a plurality of detectors disposed and configured to obtain measurement data, an image generator coupled to the plurality of detectors to reconstruct an image based on the obtained measurement data, and a source of an a priori image. The image generator is configured to generate a projector function using the obtained measurement data, modify the generated projector function using the a priori image, and reconstruct the image using the modified projector function.

According to example embodiments of the present invention, an image generator may be provided by a computing device configured to implement the image reconstruction algorithm, including generating a projector function and modifying the projector function. The image generator may be any of the example devices and systems described above, so long as the image generator is configured to perform methods of the present invention, including generating a projector function and modifying the projector function, or cause another device or system to do so.

In the system 10 shown in FIG. 1, the detectors 12 may provide the plurality of detectors for an example Bayesian approach, and the image generator may be provided by the image generator 16. A source for one or more a priori images may be provided by the detectors 12 and/or by other detectors or a separate source. Exemplary detectors (for the detectors that obtain measurement data and/or for generating an a priori image) include 2-D detectors in an insert system, such as a ring of high-resolution 2-D PET detectors inserted into a larger ring of lower-resolution 3-D detectors, multi-modality detectors, etc.

The source for a priori images may be the same detectors, devices, and/or systems for image reconstruction as those used above, and/or may be detectors and devices using other tomography techniques, in combination with suitable image generators. Other sources include add-on PET systems, such as high-resolution insert systems. However, it is to be understood that detectors or a priori image sources that can be used are not to be limited to those particular detectors, image sources, or combinations thereof that are described herein. For example, if particular embodiments of the present invention directed to imaging using a Bayesian projector do not rely on Compton kinematics collimation for providing a data channel, devices and systems according to the present invention for performing such methods need not include a detector or a priori source capable of providing Compton kinematics collimation.

Methods according to the present invention employing Bayesian projector functions may also be performed in multi-modality systems. For example, X-ray computed tomography (CT) may be used to produce an anatomical image of a subject. For PET, the radionuclide resides in tissue, and thus an a priori image may be produced using a CT image, such that the probability is zero at all the air cavities (but, not the lungs) in the body and equal (or non-zero) for all other tissue. Another application to PET is to combine measurements of PET systems (e.g., PET insert systems) that employ detectors of different sizes. For single photon emission tomography (SPECT), methods of the present invention can be used for dual collimated systems that combine mechanical collimation with electronic collimation. Additionally, in SPECT, methods of the present invention can be used to combine multiple collimation imaging systems. For example, multi-head SPECT systems that use collimators with different resolutions and sensitivities can be combined to produce images.

In a nonlimiting example method of the present invention using PET, a multichannel PET system using 3-D detectors collects two different types (channels) of measurements by coincidence collimation and Compton kinematics collimation. In coincidence collimation, as explained above, photons are detected in pairs, and the decay event is assumed to have occurred somewhere along the line between the two detected photons. In Compton kinematics collimation, a single photon is detected in a 3-D detector. The position and energies of the individual interactions in the 3-D detector are used to calculate the direction of the incident photon. Using this direction, the projector function corresponds to a cone-surface, and it is assumed that the decay event occurred somewhere on this cone-surface with equal probability.

Thus, 3-D detectors capable of measurement by coincidence collimation and Compton kinematics collimation can provide both a detector and a source of an a priori image. The Compton kinematics collimation may be used to modify the coincidence collimation. Alternatively, the coincidence collimation may be used to modify the Compton kinematics collimation. As one example, the coincidence collimation channel could be reconstructed by standard methods using the line projector function to produce a 3-D image. This 3-D image can be used to create a Bayesian projector for reconstructing the Compton kinematics collimation measurements. The projector function for Compton kinematics collimation would then be the cone-surface function (a probability function in 3-D) multiplied by the prior (treated as a probability function in 3-D). Alternatively, the Compton kinematics collimation data could be reconstructed to produce a prior used to create a Bayesian line projector function for reconstructing the coincidence collimation measurements.

An example Bayesian projector approach combining coincidence collimation channels and Compton kinematics collimation channels will now be described. A maximum likelihood estimation (MLE) approach can be used to reconstruct PET images for multi-collimation schemes. MLE effectively weights a combination of the collimation channels (such as single and coincidence photon), deconvolving the lower spatial resolution (single photon) channel to match the high-resolution (coincidence photon) channel. The weight of the low-resolution channel is proportional to the signal-to-noise after deconvolution. For sufficiently large resolution mismatch between channels, the low-resolution channel is effectively assigned a small weight. The MLE combination yields comparable spatial resolution, bias, and variance from images produced by using the high-resolution channel alone, while significantly improving the signal-to-noise ratio (SNR).

For example, in conventional image reconstruction, the line projector function assumes that the probability of the emission event is uniform along the line of response. In an example Bayesian projector approach, the non-coincident singles are used to generate a prior. Particularly, an a priori image from the non-coincident singles is used to re-weight the line projector such that the probability along the line of response is proportional to the expected activity. For example, let $g(x) \equiv g(x; T)$ be the image prior, the probability that a photon is generated over the total scan time T at the point x. The Bayesian line projector function for coincidence data is then given by $$o(y_{kl}) = \int_L p(y_{kl}, x) g(x; T) d(x; T) dx \qquad (6)$$

Similarly, a Bayesian projector function for a non-coincident singles event is given by $$s(y_i, \phi_i) = \int_C p(\phi_i, y_i, x) g(x; T) f(x; T) dx \qquad (7)$$

For multi-channel tomography, one data channel is used to generate a prior that is used to modify the projector function for the reconstruction of the other channel. For example, the non-coincidence singles data (low-resolution) can be reconstructed to produce the prior image. The Bayesian projector is then used to reconstruct the coincidence events (high-resolution), producing the final image.

Figure 7:
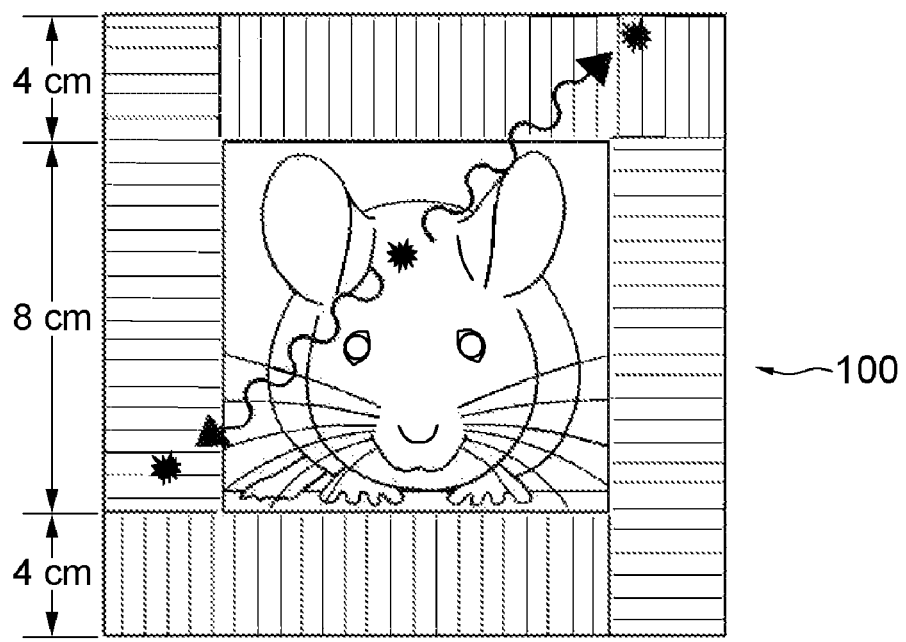
FIG. 7 shows an example small animal PET system.

In an experiment using methods of the present invention, Monte Carlo simulations were performed of PET systems built using cross-strip CZT detectors. A phantom was simulated for a box-shaped small animal PET system built using cross-strip CZT detectors. It was assumed that the detectors had a 1 mm×1 mm by 1 mm spatial resolution with 3% energy resolution FWHM for 511 keV photons. It was also assumed that the energy resolution FWHM was $3\% * \sqrt{511/e_{pho}}$ where $e_{pho}$ is the energy of the photon in keV. A schematic of this detector arrangement 100 is shown in FIG. 7. The system has an 8 cm×8 cm transaxial FOV. The axial length of the simulated system was 2 cm. Data acquisition was simulated for 7 non-overlapping bed positions. Hits files were generated of all the individual interactions within the detectors. These files were processed to simulate the performance of the system.

Figure 8A:
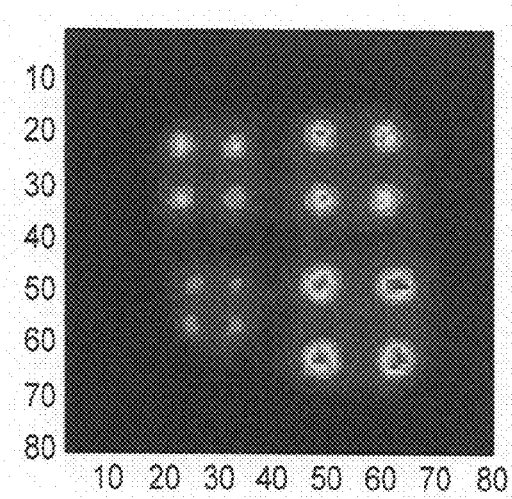
FIGS. 8A-8B show reconstructed images of a phantom with 16 spherical sources using coincidence data and non-coincident singles data respectively.
Figure 8B:
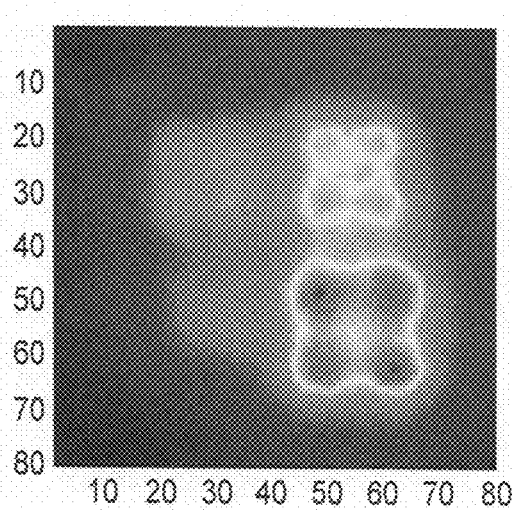

A resolution phantom was simulated as a 5 cm diameter, water-filled cylinder with a single plane of spherical sources divided into four quadrants. The spherical sources in each quadrant were 1, 1.25, 1.5, and 1.75 mm in diameter with center-to-center separation that was twice the diameter of the spheres. A total of 0.2 mCi of activity was simulated. Images reconstructed using the coincidence data and non-coincident singles data are shown in FIGS. 8A-8B.

Figure 9A:
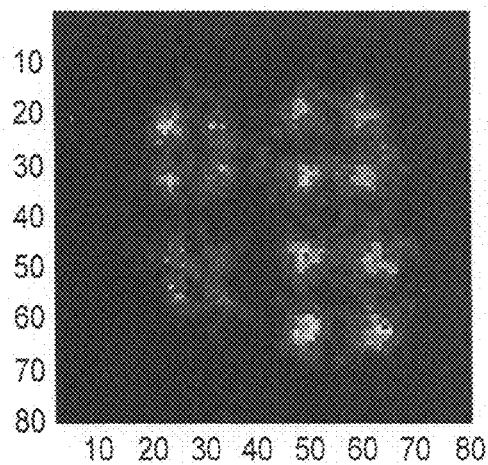
FIGS. 9A-9D show images reconstructed by various methods, where
Figure 9B:
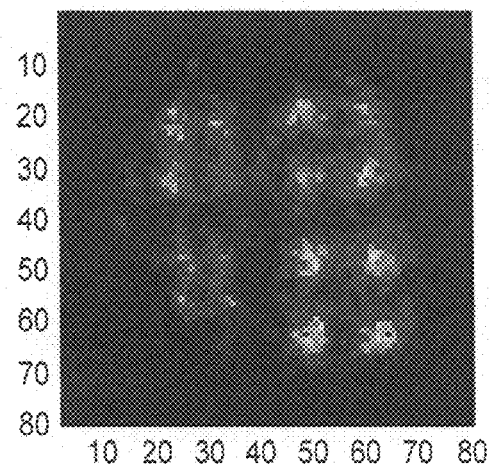
Figure 9C:
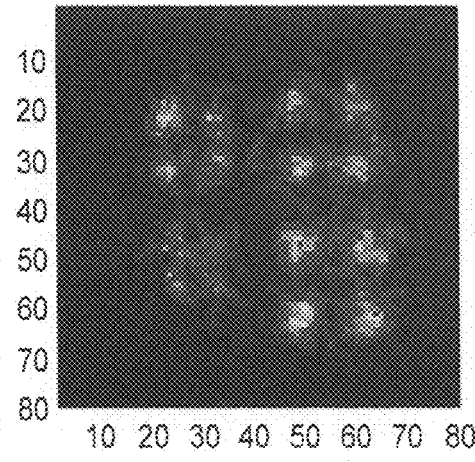
Figure 9D:
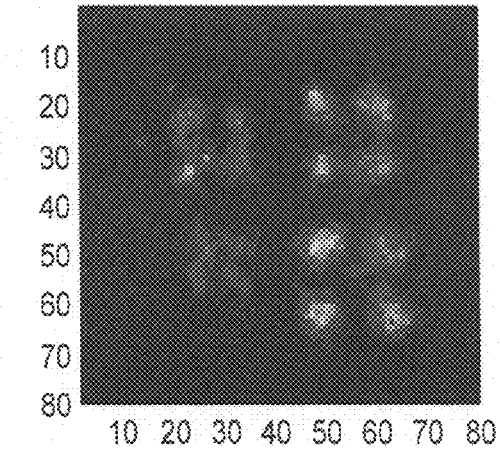
Figure 10A:
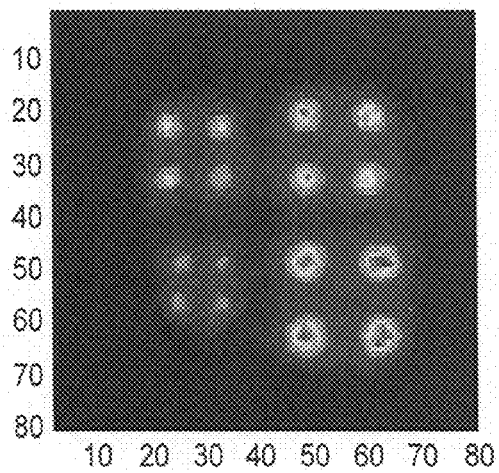
FIGS. 10A-10D show mean reconstructed images, where
Figure 10B:
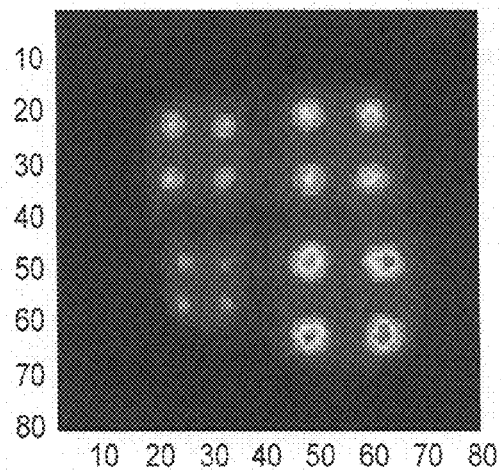
Figure 10C:
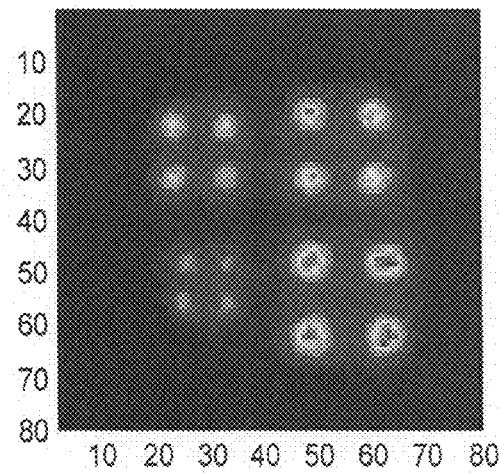
Figure 10D:
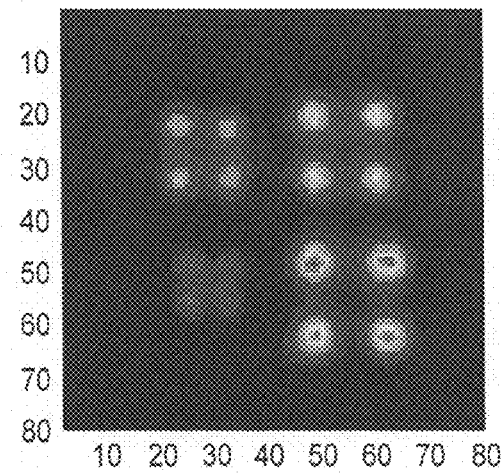

Images reconstructed using the same data set by example methods are shown in FIGS. 9A-9D. Reconstruction using only the coincidence data is shown in FIG. 9A. There is no discernable difference in the image quality between the simultaneous channel (FIG. 9B), sequential channel (FIG. 9C), and coincidence-only (FIG. 9A) images. The noise structure for the simultaneous channel approach differs from the coincidence-only reconstructed image. The noise structure is visually identical for sequential channel and coincidence-only image reconstruction. The Bayesian projector method (FIG. 9D) produced an image with improved contrast against the background compared to the other methods.

The mean and variance images were computed from twenty simulated trials for each of the methods. The mean images are shown in FIGS. 10A-10D. The image quality is comparable for coincidence-only (FIG. 10A), simultaneous channel (FIG. 10B), and sequential channel (FIG. 10C) images. The mean reconstructed image for the Bayesian projector method (FIG. 10D) shows a larger partial volume effect for the 1 mm spheres.

The variance-to-signal ratio was computed from 20 trials for regions of interest (ROI) drawn around the spheres on the center plane. The results are as follows: the coincidence-only reconstruction method exhibited a variance-mean ratio of 1.00, while the simultaneous channel, sequential channel, and Bayesian projector methods exhibited variance-mean ratios of 0.93, 1.01, and 1.35, respectively. The simultaneous channel methods showed the best performance, and the Bayesian projector approach had the worst performance.

Figure 11:
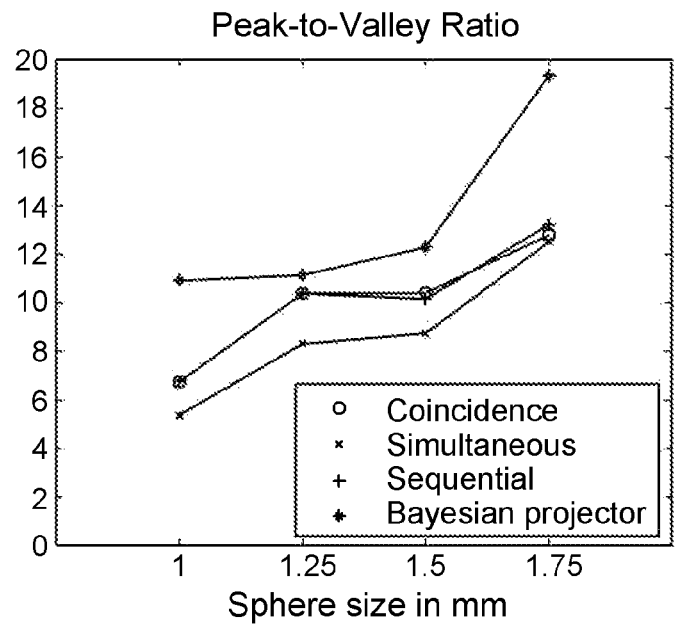
FIG. 11 shows peak-to-valley ratios for four reconstruction methods.

The peak-to-valley ratio was measured from the mean images and plotted for the different reconstruction methods and shown in FIG. 11. The peak-to-valley ratios are shown for the various sized spheres. The Bayesian projector approach had a better peak-to-valley ratio for all sized spheres.

Figure 12:
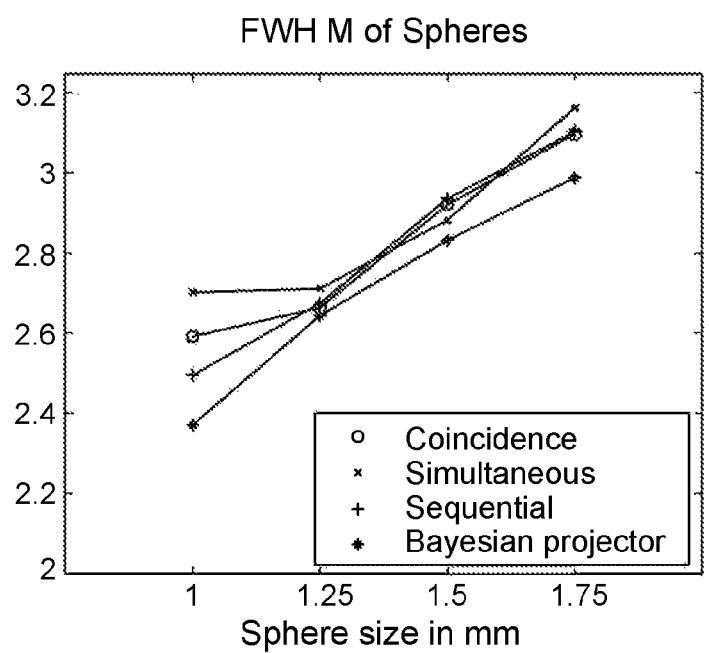
FIG. 12 shows a full width at half maximum (FWHM) of a Gaussian function fitted to profiles drawn through spheres reconstructed though various methods.

The resolution for the various methods was calculated by drawing profiles through the various sized spheres in the mean reconstructed image. A Gaussian function was fitted to the profiles, and the full width at half maximum (FWHM) for the various sized spheres is plotted in FIG. 12. The Bayesian projector methods showed better contrast and resolution for all size spheres than the other methods, with a slight loss in signal-to-noise ratio. However, the images produced by the Bayesian projector function depend on the quality of the image prior and the phantom characteristics.

The low-resolution nature of this image leads to partial volume effects for the 1 mm spheres. This partial volume effect results in a lower probability of counts placed in the 1 mm spheres by the Bayesian projector function. Consequently, the reconstructed activity in the 1 mm spheres was biased down proportionately to the partial volume effect of the reconstructed image used to generate the prior. Effectively, counts were "stolen" from the 1 mm spheres and placed in the other spheres. Misplaced counts could explain the observed decrease in the signal-to-noise ratio for the Bayesian projector method.

Additional embodiments of the invention use priors generated by reconstructing images from high-spatial resolution coincidence data followed by post-reconstruction smoothing with a spatially varying 3-D filter function. Methods of the invention may also use a gradient anisotropic filter. According to another embodiment of the present invention, an example 3-D OS-EM algorithm is used with a prior-weighted Compton collimated projector to reconstruct the single photon data and the conventional (unweighted) projector to reconstruct the coincidence photon data.

In conventional image reconstruction, the emission probability is uniform along a line of response (LOR). In an example Bayesian projector method, by contrast, the probability along the LOR is weighted by a prior image; particularly, the LOR probability passing through regions of high activity in the prior will have high probability relative to regions of low activity in the prior.

In the example Bayesian method described above, a low-spatial resolution Compton collimated single-photon channel is used to produce a prior for weighting the high-resolution coincidence photon channel to provide a qualitative improvement in visual quality. In another example method, priors generated from the higher resolution coincidence photon data are used for reconstructing the low resolution single photon channel.

Figure 13:
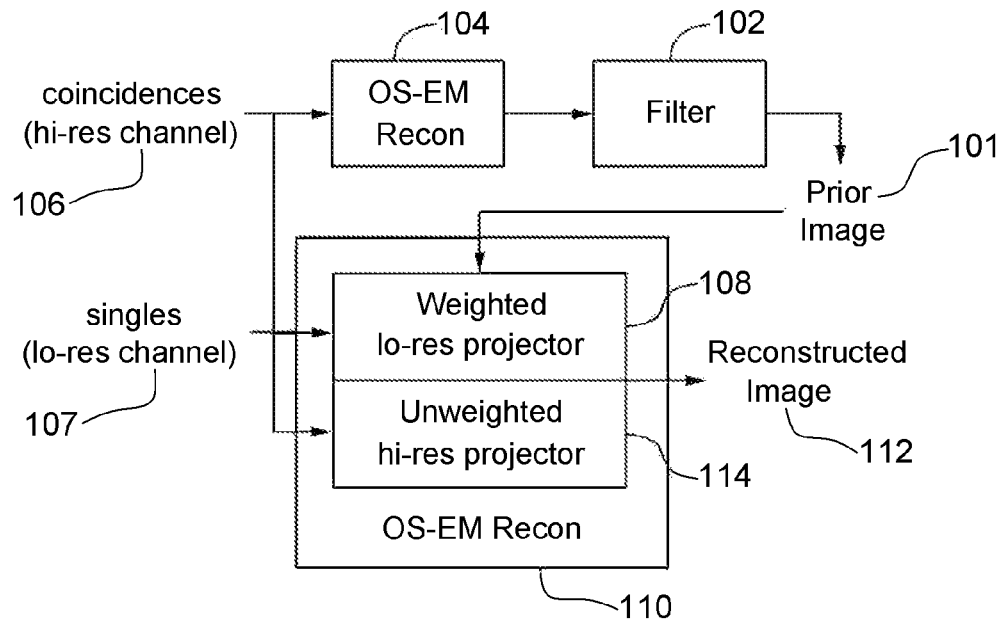
FIG. 13 shows an example reconstruction algorithm using a Bayesian approach, according to another embodiment of the present invention.

An example reconstruction algorithm for the latter method is shown in FIG. 13. An a priori image 101 is produced by filtering 102 a higher-resolution image 104. This higher-resolution image is reconstructed from the coincidence photons 106. The prior 101 is used to weight a Compton collimated single-photon channel (lower-resolution channel) 107, providing a weighted low-resolution channel 108. In the example method, the list-mode OS-EM algorithm 110 is used to iteratively calculate an MLE solution 112 by simultaneous reconstruction of both the (unweighted) high-resolution channel 114 and the weighted low-resolution channel 108. A nonlimiting example uses a list-mode 3-D OS-EM algorithm with 5 iterations and 10 subsets/iteration—the minimum number of iterations-subsets to achieve 9:1 sphere:background ratio for 1.75 mm spheres.

In an example method, a 3-D spatially-varying filter was used:

$$y(i, j, k) = \sum_l \sum_m \sum_n I_A(i, j, k, l, m, n) \cdot h(i-l, j-m, k-n) \quad (8)$$

$$x(i-l, j-m, k-n)$$

where h is the filter kernel, x and y are the images before and after filtering, and the indicator function $I_A$ is defined over the interval $$A = \{|x(i,j,k) - x(i-l, j-m, k-n)| < \alpha \sqrt{x(i,j,k)} + \epsilon\} \quad (9)$$

The parameter α tunes the filtering to the expected lesion contrast. An example image using both unweighted coincidences and weighted Compton collimation photons was produced by one iteration with five subsets of the 3D OS-EM algorithm (for 9:1 sphere:background ratio, 1.75 mm spheres).

A second filter that may also be used is a gradient anisotropic non-linear diffusion filter. For example, an iterative filter may be created from a discrete diffusion equation. Each time step in the diffusion equation corresponds to an iteration of the filter. The total intensity of all pixels in the image was conserved at every time step with pixel intensity flowing to adjacent pixels. The diffusion rate and number of iterations can be used to control the degree of smoothness in the filtered image, with more iterations and larger diffusion rates producing smoother images. An example discrete diffusion equation is given by $$\frac{u_{i,j}^{t+\Delta t} - u_{i,j}^t}{\Delta t} = \frac{1}{\Delta x}\left[E_{i,j}^r \nabla_E u_{i,j}^t - W_{i,j}^t \nabla_W u_{i,j}^t\right] + \frac{1}{\Delta y}\left[N_{i,j}^t \nabla_N u_{i,j}^t - S_{i,j}^t \nabla_S u_{i,j}^t\right] \quad (10)$$

where u is the intensity of the pixel at (i,j) at time step t. The diffusion coefficients in the north, east, south, and west directions are given by N, E, S, and W at pixel (i,j), respectively, and take the form of $$D_{i,j}^t = g\left(\left|\nabla_D u_{i,j}^t\right|^2\right) \quad (11)$$

where D specifies the direction (N, E, S, or W). The Perona-Malik filter (e.g., as described in S-J Park et al, "A prototype of very high resolution small animal PET scanner using silicon pad detectors," Nuc. Instrum. Meth. Phys. Res. A, 570 (3), pp. 543-555, 2007) varies the diffusion coefficient, 1 within the interior of regions and 0 at the boundaries, in order to smooth the image while preserving edges.

For Compton collimation, the lines of response form the surface of a cone as shown in FIG. 3. The measured energy of the first interaction is used to determine the photon angle φ relative to the cone axis, the line defined by the first two interactions. Uncertainty in the measured energy and the positioning of the cone axis leads to angular blurring. The angular blurring varies depending on the energy of the first scattering interaction and the distance between the interactions. Low-energy and high-energy interactions will have the poorest angular resolution. Also, the closer the two interactions are to each other, the worse the angular resolution.

Event filtering was used to improve the spatial resolution of Compton collimation. Since angular resolution degrades rapidly below a 15-20 degree scatter angle, single photons with detector scatter below 20 keV were not used to improve the angular resolution. A minimum interaction distance threshold was used to reduce the uncertainty of the cone axis position. Single photons were used only when the distance between the first two interactions was greater than 1 cm. At 1 cm separation between interactions, a 1 mm voxel size results in an angular error variance of 3 degrees if the discretization error is uniformly distributed. Event filtering improves angular resolution, but also reduces the single photon sensitivity.

Figure 14:
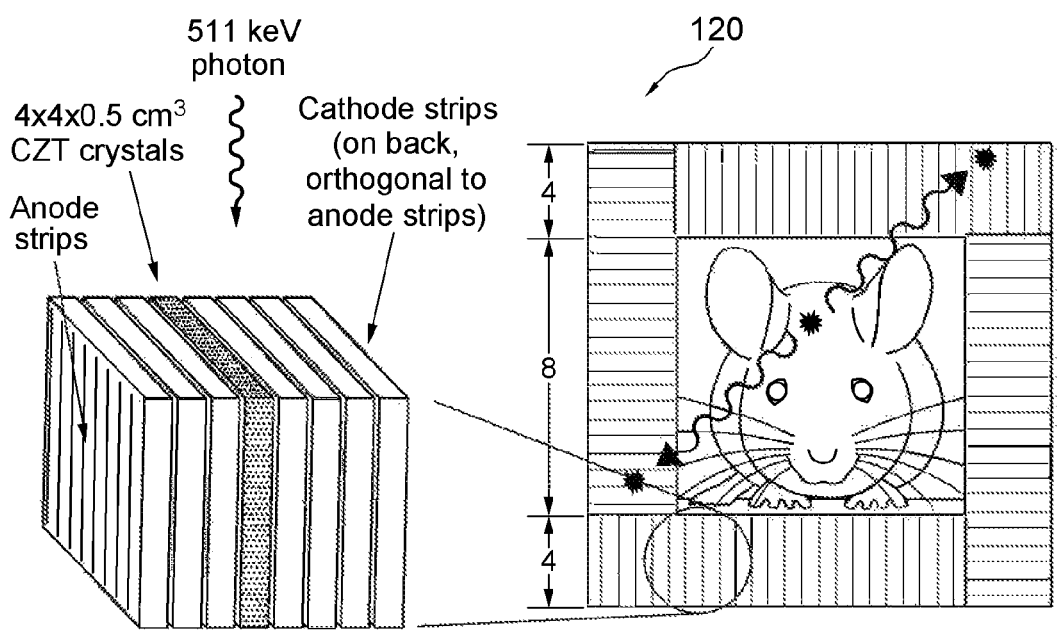
FIG. 14 shows an example detector arrangement used in example methods illustrating the Bayesian approach shown in FIG. 13, with an individual detector enlarged for clarity.

In a Monte Carlo simulation of an example system, an 8×8×2 cm³ box-shaped system 120 as shown in FIG. 14 was simulated using 4×4×1/2 cm³ 3-D CZT detectors with cross-strip anodes and cathodes. This example detector can position Compton scattering interactions within the detector in three dimensions with 1.5-2.5% FWHM at 511 keV energy resolution. As shown in FIG. 14, the detector is oriented in an edge-on configuration for higher sensitivity so that incoming photons see a minimum of 4 cm of CZT. Simulations were performed using an idealized energy resolution model $$\Delta e = 0.025\sqrt{511e} \quad (12)$$

where e is the energy of the interaction in keV. This idealized energy resolution model assumes noiseless readout electronics. A more realistic model was also simulated, which assumed the readout electronics provided an additional keV FWHM Gaussian noise source to each energy measurement independent of the interaction energy.

Figure 15A:
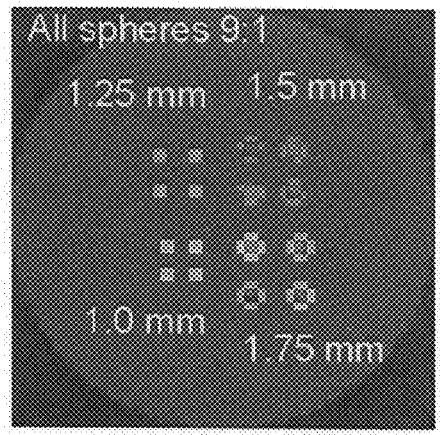
FIGS. 15A-15B show two digital phantoms of a cylinder and spheres used in an experiment, where
Figure 15B:
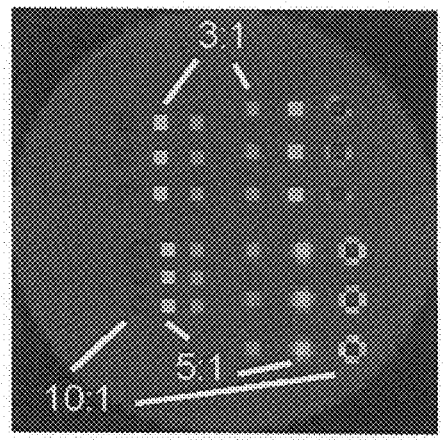

Two digital phantoms were simulated, as shown in FIGS. 15A-B. The phantoms were each 7.5 cm high by 3 cm diameter cylinders with 1, 1.25, 1.5, and 1.75 mm diameter spheres separated by twice the diameter organized in four different quadrants in the center slice of the cylinder. A total of 500 μCi total activity was scanned with 5 bed positions.

Phantom 1 was a 9:1 sphere:cylinder concentration (activity) ratio with idealistic energy resolution and 30 sec/bed position. After event filtering, 11 million Compton collimation single photons and 10 million coincidence photons were used for image reconstruction. A 10 ns coincidence time window and a 10% energy window at 511 keV for coincidence and single photons were used. The energy resolution of the CZT detector was 2.5% at 511 keV. Since multiple interactions can occur, the energy window was chosen to be larger than is conventionally used in PET.

In phantom 2, the spheres are organized in three columns with 10:1, 5:1, and 3:1 sphere-to-cylinder activity ratios in the outer, middle, and inner columns, respectively. The scan time was 60 sec/bed position using the more realistic energy resolution model. After event filtering, the simulation yielded 27 million Compton collimated single photon events and 21 million coincidence photons. Setting the minimum interaction distance threshold threshold to zero, the number of available single events was 124 million. Thus, event filtering reduced the number of usable single photon events by approximately 80%.

Figure 16A:
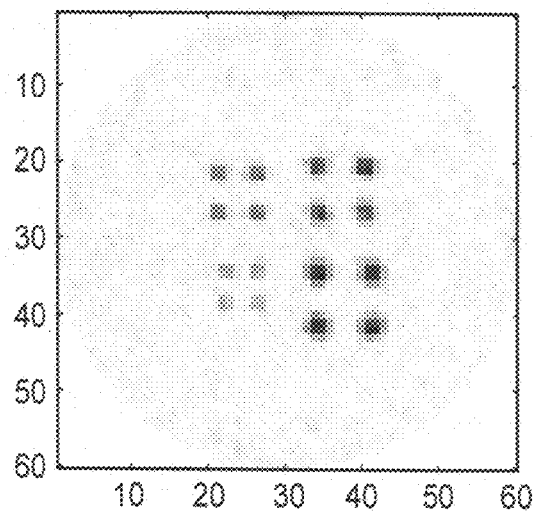
FIGS. 16A-16B show reconstructed images for phantom 1, where
Figure 16B:
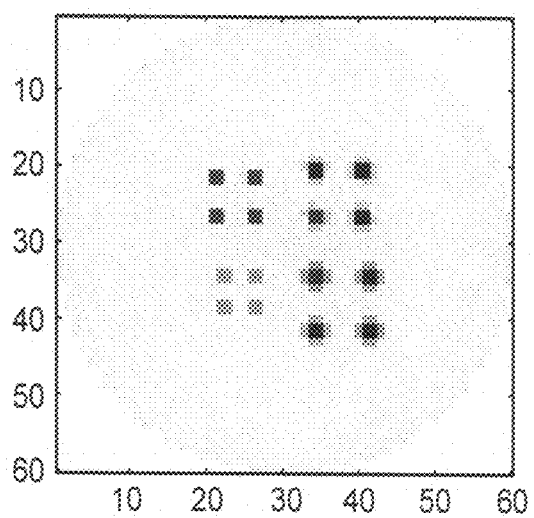

Results are shown in FIGS. 16A-B. FIG. 16A shows the reconstructed image from coincidence events for phantom 1. Normalization/sensitivity correction was not used in the image reconstruction. The list-mode OS/EM algorithm was used with 2 iterations, with 10 subsets per iteration. Subsets were divided by time with an equal number of counts for each subset. The image in FIG. 16B was produced by combining coincidence events and singles using 1 iteration, with 5 subsets. The Bayesian prior was produced from coincidence data by using 5 iterations and 10 subsets/iteration. The two filters described above by equations (8) and (9) were used.

Using the Bayesian projector to reconstruct singles and coincidence events improved the SNR in a region of interest (ROI) drawn within the cylinder by a factor of 10 for similar recovered contrast of the spheres. The SNR in the spheres also improved by approximately 20%, as measured by drawing ROIs in the center of every sphere.

Figure 17A:
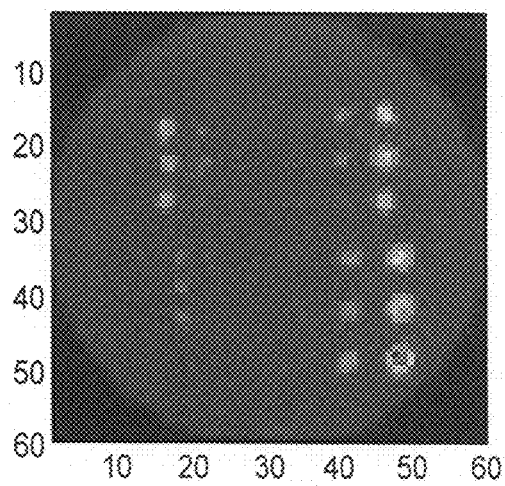
FIGS. 17A-17B show reconstructed images for phantom 2 with a more realistic energy resolution model, where
Figure 17B:
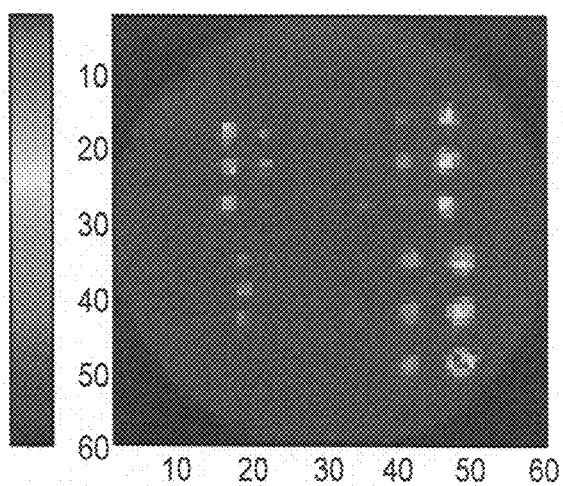

The reconstructed images with sensitivity correction for phantom 2 (with more realistic energy blur model) are shown in FIGS. 17A-B. A Monte Carlo simulation with 30 minutes of simulated scan time was used to calculate the sensitivity correction. Gaussian smoothing was used. The image reconstructed from coincidence events is shown in FIG. 17A. This image was produced by 2 iterations, with 10 subsets per iteration. The image in FIG. 17B was reconstructed using the Bayesian projector and 2 iterations, with 6 subsets per iteration from combining coincidence events and singles. The Bayesian prior was produced from coincidence data using 2 iterations, with 10 subsets per iteration. The Perona-Malik filter was used for de-noising the prior.

Figure 18A:
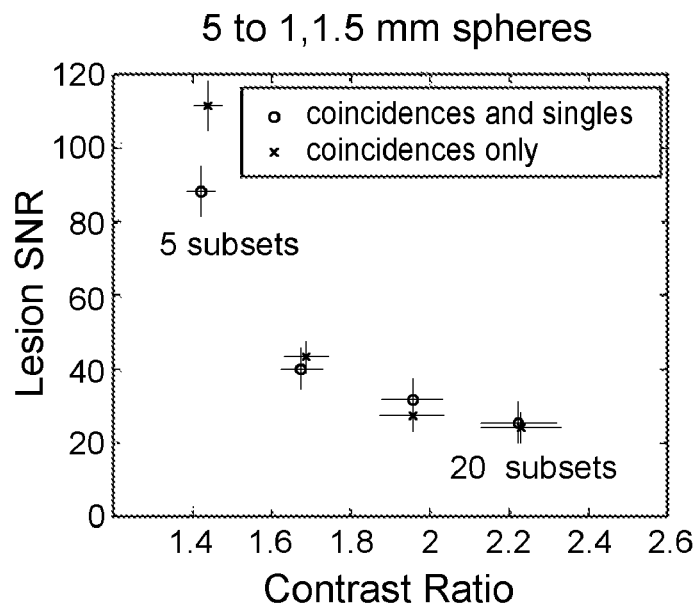
Figure 18B:
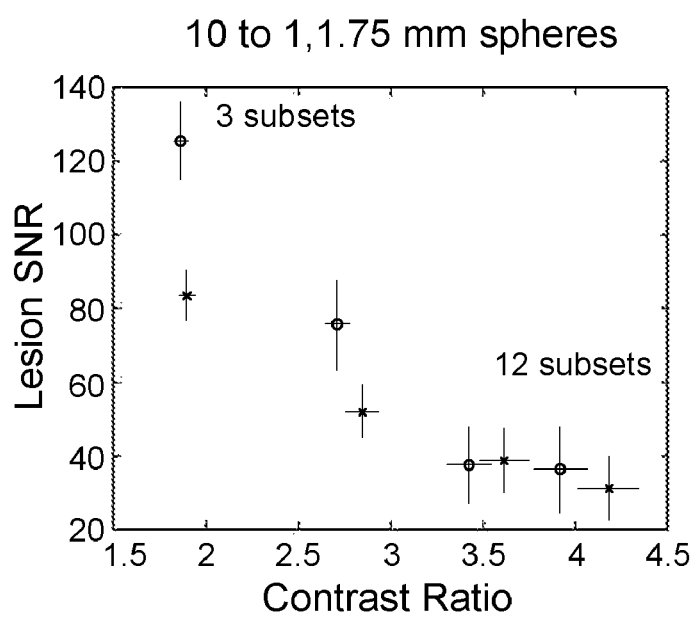

There was no significant improvement in the SNR for the spheres at comparable contrast as shown in FIGS. 18A-B. The SNR in the background cylinder ROI was improved by about 20%.

Figure 19A:
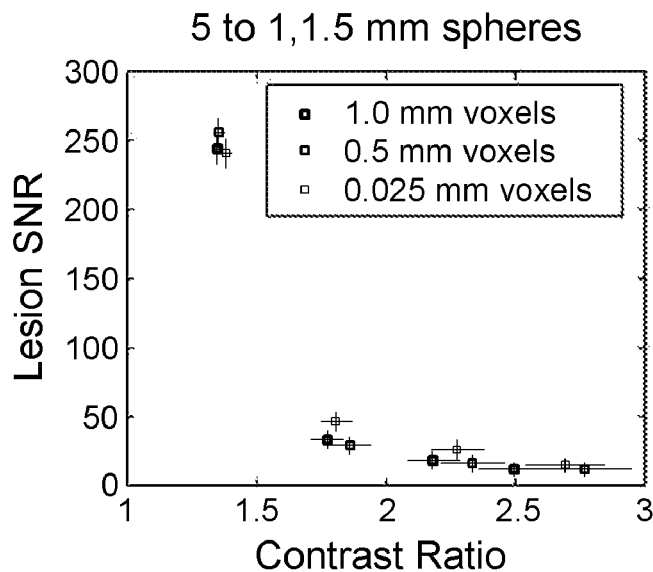
FIGS. 19A-19B are plots of sphere SNR versus contrast ratio for different iteration-subsets for coincidence and singles reconstruction using the Bayesian projector with detector voxel sizes of 0.025, 0.5, and 1 mm, where
Figure 19B:
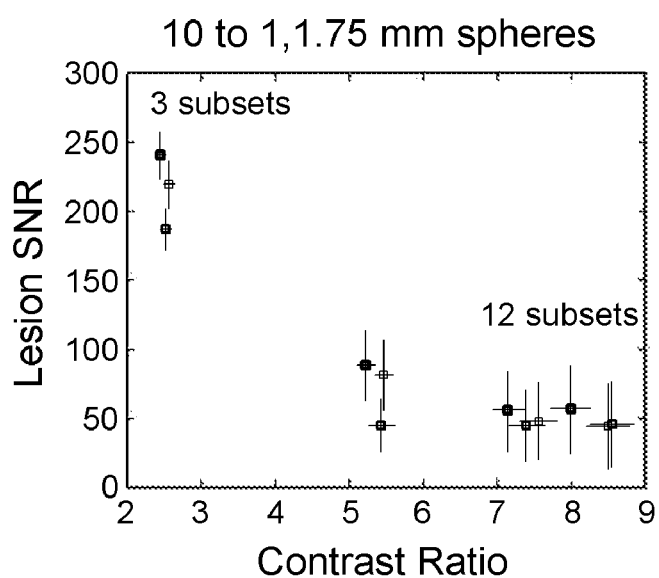

To assess the effect of detector voxel size, the voxel size was simulated at 0.025 mm, 0.5 mm, and 1.0 mm. The results of the sphere (lesion) SNR vs. contrast ratio for various iteration-subsets is shown in FIGS. 19A-B. There was no significant difference in reconstructed image quality for the various detector voxel sizes, suggesting that energy resolution was the dominant component of angular blurring for Compton collimation. Improved angular resolution of Compton collimation should in turn increase the benefits of imaging single photons.

It will be understood that, though a small animal system such as that used in experiments described herein has high coincidence sensitivity and low single photon sensitivity, a human imaging system would have significantly higher relative single photon count rate and could yield improved image quality for combined coincidence and Compton collimation PET. With a large number of single photons, more aggressive event filtering could be used to improve Compton collimation spatial resolution.

Significant advantages of embodiments of the present invention include reduction of scanning time to increase patient throughput, and improve sensitivity, quantification, and image quality (as defined by signal-to-noise ratio, resolution, contrast, and contrast recovery). It will be appreciated that various methods are possible for combining coincidence and Compton kinematics collimation via a Bayesian projector, and the present invention is not be limited to the particular methods described herein. The filters described herein are also intended to be nonrestrictive. It will further be appreciated that methods of imaging using Bayesian multi-collimation schemes are not limited to combining coincidence and Compton kinematics collimation. Applications of the present invention include nuclear imaging modalities such as (but not limited to) PET.

While various embodiments of the present invention have been shown and described, it should be understood that other modifications, substitutions, and alternatives are apparent to one of ordinary skill in the art. Such modifications, substitutions, and alternatives can be made without departing from the spirit and scope of the invention, which should be determined from the appended claims.

Various features of the invention are set forth in the appended claims.

What is claimed is:

1. A method for producing an image comprising:
   obtaining measurement data for a coincidence photon event;
   generating a line projector function based on the obtained measurement data;
   obtaining additional measurement data for a single detected photon from an event other than the coincidence photon event;
   generating a cone-surface projector function based on the additional measurement data;
   combining data from said generated line projector function and said generated cone-surface projector function;
   reconstructing an image using said combined data from said line projector function and said generated cone-surface projector function.

2. The method of claim 1, wherein said generating the cone-surface projector function uses Compton kinematics collimation.

3. The method of claim 1, wherein said generated line projector function provides a coincidence collimation channel and said generated cone-surface projector function provides a Compton kinematics collimation channel;
   wherein said reconstructing an image further comprises:
   combining data from the coincidence collimation channel and the Compton kinematics collimation channel.

4. The method of claim 3, wherein said combining comprises using data from the coincidence collimation channel simultaneously with data from the Compton kinematics collimation channel.

5. The method of claim 3, wherein said combining comprises using data from the coincidence collimation channel sequentially with data from the Compton kinematics collimation channel.

6. The method of claim 3, wherein said combining comprises using data from the coincidence collimation channel to reweight the cone-surface projector function.

7. The method of claim 3, wherein said combining comprises using data from the Compton kinematics collimation channel to reweight the line projector function.

8. The method of claim 1, wherein said obtaining measurement data for a coincidence photon event comprises:
   producing a photon interaction in each of a pair of detectors;
   for each of the pair of detectors, determining a position and energy of the produced photon interaction.

9. The method of claim 1, wherein said obtaining additional measurement data for the single detected photon comprises:
   producing at least two photon interactions in a detector;
   determining a position and energy of the produced at least two photon interactions.

10. The method of claim 1, wherein said reconstructing an image uses an image reconstruction algorithm.

11. A system for radiation-based imaging comprising:
   a plurality of 3-D detectors disposed with respect to a source of emitted photons to receive the emitted photons and produce interactions, the interactions detecting at least coincidence photons from a coincidence photon event and, additionally, single detected photons from events other than the coincidence photon event;
   an image generator coupled to said plurality of 3-D detectors to receive a position and energy for the produced interactions and reconstruct an image;
   said image generator being configured to generate a line projector function based on the detected coincidence photons and a cone-surface projector function based on the additional single detected photons, combine data from the generated line projector function and the generated cone-surface projector function, and reconstruct an image using the combined data from the generated line projector function and the cone-surface projector function.

12. The system of claim 11, wherein the generated line projector function provides a coincidence collimation channel and the generated cone-surface projector function provides a Compton kinematics collimation channel;
   wherein reconstructing the image further comprises:
   combining data from the coincidence collimation channel and the Compton kinematics collimation channel.

13. The system of claim 12, wherein the combining comprises at least one of using data from the coincidence collimation channel simultaneously with data from the Compton kinematics collimation channel, and using data from the coincidence collimation channel sequentially with data from the Compton kinematics collimation channel.

14. The system of claim 12, wherein the combining comprises at least one of using the coincidence collimation channel to reweight the cone-surface projector function, and using data from the Compton kinematics collimation channel to reweight the line projector function.

15. The system of claim 11, wherein said plurality of 3-D detectors comprises cadmium zinc telluride (CZT) detectors.

16. The system of claim 11, wherein said image generator comprises a computing device.

17. An image generator comprising:
   a computing device configured to perform a method comprising:
   obtaining measurement data for a coincidence photon event;
   generating a line projector function based on the obtained measurement data;
   obtaining additional measurement data for a single detected photon from an event other than the coincidence photon event;
   generating a cone-surface projector function based on the additional measurement data;
   combining data from said generated line projector function and said generated cone-surface projector function; and
   reconstructing an image using said combined data from said line projector function and said generated cone-surface projector function.

18. The image generator of claim 17, wherein said obtaining measurement data for a coincidence photon event comprises:
   receiving a signal generated from a produced photon interaction in each of a pair of detectors;
   for each of the pair of detectors, determining a position and energy of the produced photon interaction.

19. An apparatus for controlling a computing device comprising:
   a non-transitory computer-readable medium containing computer-readable instructions that, when read, cause a computer to perform a method comprising:
   obtaining measurement data for a coincidence photon event;
   generating a line projector function based on the obtained measurement data;
   obtaining additional measurement data for a single detected photon from an event other than the coincidence photon event;
   generating a cone-surface projector function based on the additional measurement data;
   combining data from said generated line projector function and said generated cone-surface projector function; and
   reconstructing an image using said combined data from said line projector function and said generated cone-surface projector function.

20. the apparatus of claim 19, wherein said obtaining measurement data for a coincidence photon event comprises:
   receiving a signal generated from a produced photon interaction in each of a pair of detectors;
   for each of the pair of detectors, determining a position and energy of the produced photon interaction.

* * * * *

UNITED STATES PATENT AND TRADEMARK OFFICE
CERTIFICATE OF CORRECTION

PATENT NO. : 8,183,531 B2
APPLICATION NO. : 12/154206
DATED : May 22, 2012
INVENTOR(S) : Garry Chinn et al.

Page 1 of 1

It is certified that error appears in the above-identified patent and that said Letters Patent is hereby corrected as shown below:

In the Specification:

Col. 1, lines 16-19   Please delete "This invention was made with Government assistance under National Institutes of Health (NIH) Grant Nos. CA119056 and EB003283. The Government has certain rights in the invention." and insert --This invention was made with Government support under contracts CA119056 and EB003283 awarded by the National Institutes of Health. The Government has certain rights in the invention.-- therefor.

Signed and Sealed this
Tenth Day of May, 2016

Michelle K. Lee
*Director of the United States Patent and Trademark Office*